US009067056B2

(12) United States Patent  (10) Patent No.: US 9,067,056 B2
Sage  (45) Date of Patent: Jun. 30, 2015

(54) LEAD SPACER TOOL

(75) Inventor: Shahn S. Sage, Andover, MN (US)

(73) Assignee: Greatbatch Ltd., Clarence, NY (US)

( * ) Notice: Subject to any disclaimer, the term of this patent is extended or adjusted under 35 U.S.C. 154(b) by 211 days.

(21) Appl. No.: 13/490,822

(22) Filed: Jun. 7, 2012

(65) Prior Publication Data

US 2013/0331856 A1  Dec. 12, 2013

(51) Int. Cl.
*A61N 1/05* (2006.01)
*A61B 17/32* (2006.01)
*A61B 17/3209* (2006.01)

(52) U.S. Cl.
CPC .............. *A61N 1/05* (2013.01); *A61B 17/3209* (2013.01); *A61B 17/320016* (2013.01); *A61N 1/0553* (2013.01); *A61B 2017/320056* (2013.01)

(58) Field of Classification Search
CPC ............................. A61N 1/0551; A61N 1/0553
USPC ..................................................... 607/45–46
See application file for complete search history.

(56) References Cited

U.S. PATENT DOCUMENTS

| 6,512,958 | B1 | 1/2003 | Swoyer et al. |
| 8,014,873 | B2 | 9/2011 | Jones et al. |
| 2005/0288758 | A1* | 12/2005 | Jones et al. .................... 607/116 |
| 2006/0149335 | A1* | 7/2006 | Meadows ......................... 607/45 |
| 2007/0093852 | A1 | 4/2007 | Greenberg et al. |
| 2010/0030227 | A1 | 2/2010 | Kast et al. |
| 2011/0015646 | A1 | 1/2011 | North |
| 2012/0016378 | A1* | 1/2012 | Pianca et al. .................... 606/129 |

* cited by examiner

*Primary Examiner* — Paula J Stice
(74) *Attorney, Agent, or Firm* — Michael P. Horvath

(57) ABSTRACT

A combined dissection tool and blank for implanting a paddle lead having an electrode portion and a lead body. The combined dissection tool and blank includes a blank with a maximum cross-sectional area substantially equal to a maximum cross sectional area of the electrode portion of the paddle lead. An elongated body portion is attached to the blank. A guide wire extends through the body portion substantially to a distal end of the blank. The guide wire provides sufficient column strength to separate fatty tissue to create a space for receiving the paddle lead.

28 Claims, 7 Drawing Sheets

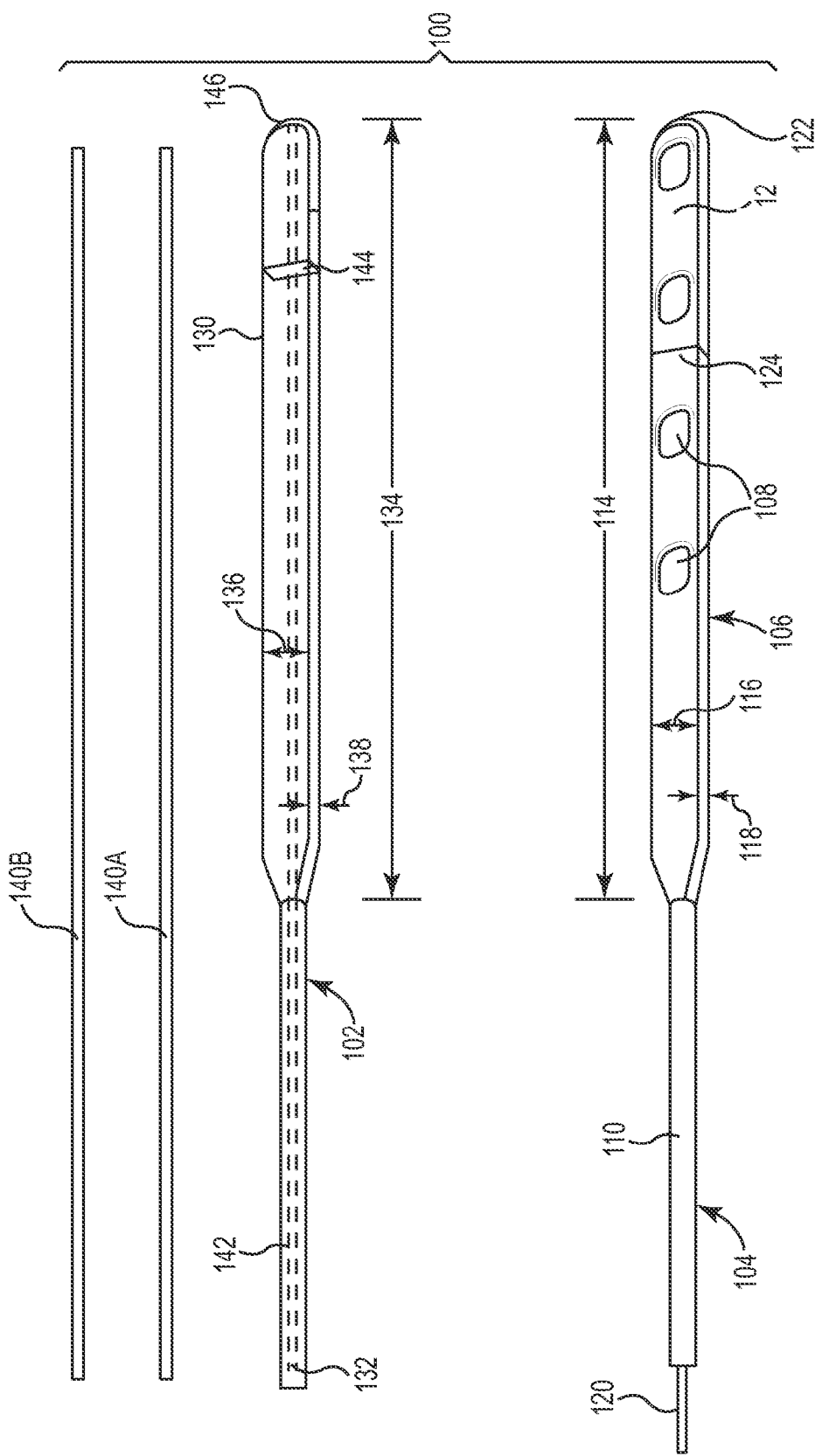

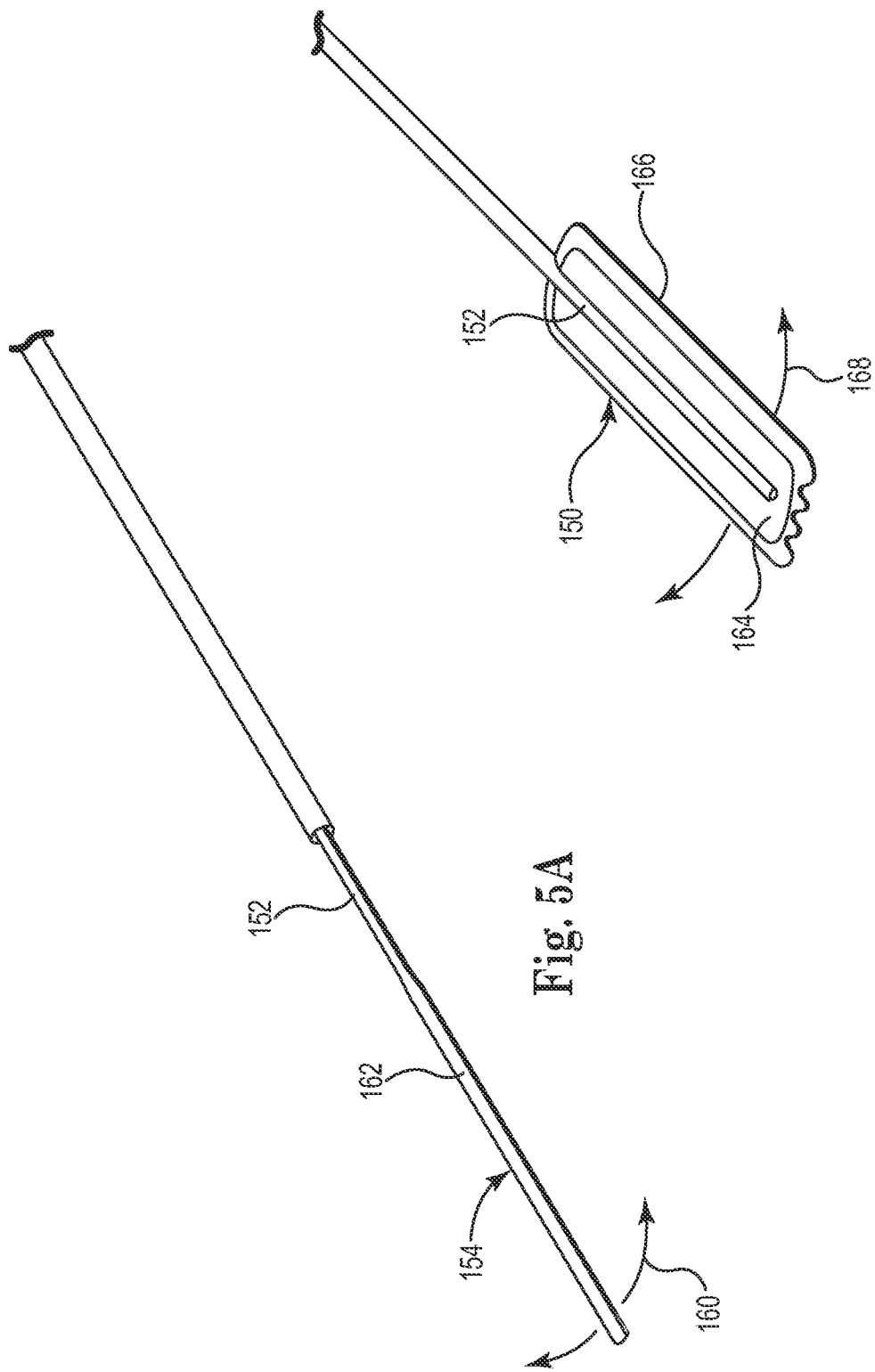

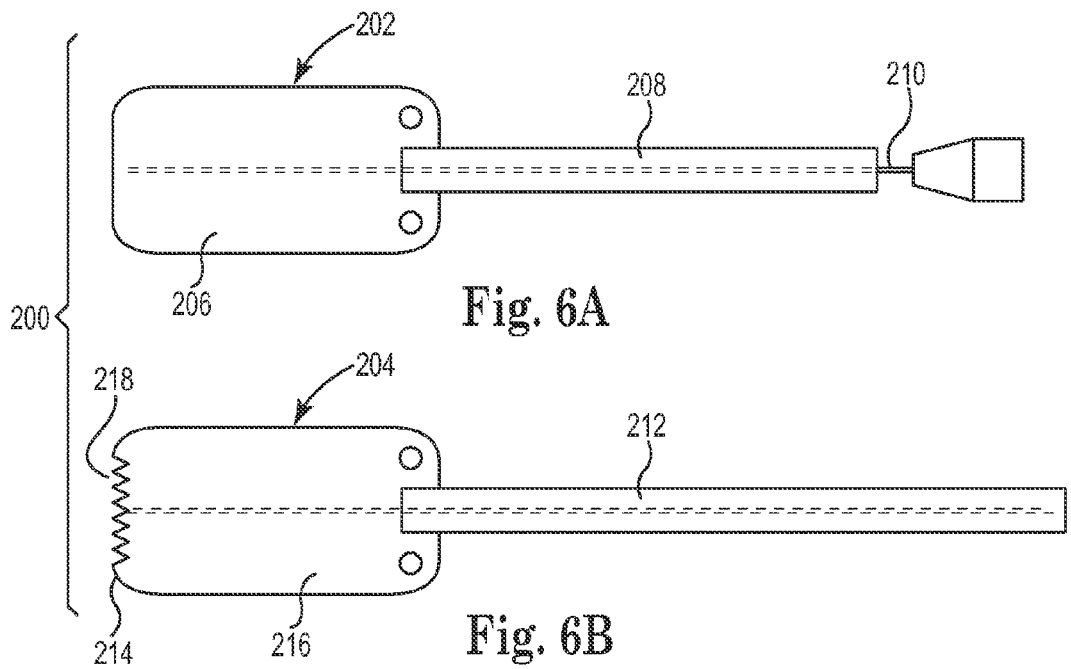
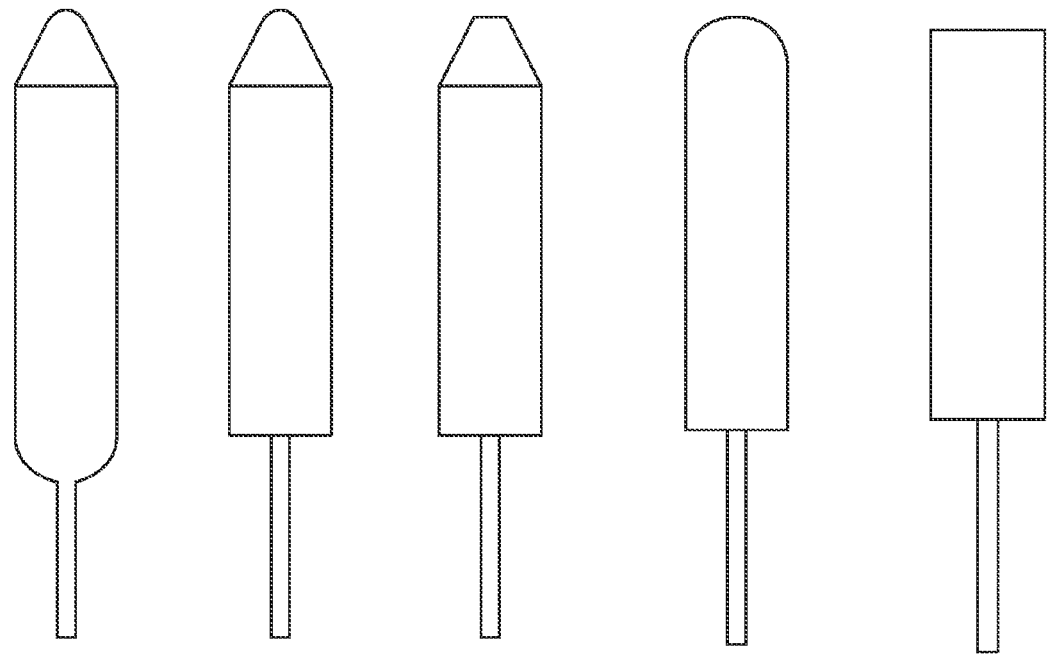

LEAD SPACER TOOL

FIELD

The present disclosure is directed to a combination dissection tool and blank that has a maximum cross-sectional area substantially the same as a maximum cross-sectional area of the paddle lead being implanted, reducing the risk of creating an oversized space.

BACKGROUND

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Peripheral Nerve Stimulation (PNS) systems have demonstrated efficacy in the treatment of chronic pain syndromes and incontinence, and a number of additional applications are currently under investigation. Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more therapy delivery elements implanted at the desired stimulation site and an implantable neurostimulator, such as an implantable pulse generator (IPG), implanted remotely from the stimulation site, but coupled either directly to the therapy delivery elements or indirectly to the therapy delivery elements via one or more extensions in cases where the length of the therapy delivery elements is insufficient to reach the IPG. Electrical pulses can be delivered from the neurostimulator to the therapy delivery elements to stimulate the tissue and provide the desired efficacious therapy to the patient.

In the context of an SCS procedure, one or more therapy delivery elements are introduced through the patient's back into the epidural space under fluoroscopy, such that the electrodes carried by the leads are arranged in a desired pattern and spacing to create an electrode array. The specific procedure used to implant the therapy delivery elements will ultimately depend on the type of therapy delivery elements used. Currently, there are two types of commercially available therapy delivery elements: a percutaneous lead and a paddle lead.

A percutaneous lead includes a cylindrical body with ring electrodes, and can be introduced into contact with the affected spinal tissue through a Touhy-like needle, which passes through the skin, between the desired vertebrae, and into the epidural space above the dura layer. For unilateral pain, a percutaneous lead is placed on the corresponding lateral side of the spinal cord. For bilateral pain, a percutaneous lead is placed down the midline of the spinal cord, or two percutaneous leads are placed down the respective sides of the midline. In many cases, a stylet, such as a metallic wire, is inserted into a lumen running through the center of each of the percutaneous leads to aid in insertion of the lead through the needle and into the epidural space. The stylet gives the lead rigidity during positioning, and once the lead is positioned, the stylet can be removed after which the lead becomes flaccid.

Paddle leads have a paddle-like configuration and typically possess multiple electrodes arranged in one or more independent columns. Paddle leads provide a more focused energy delivery than percutaneous leads because electrodes may be present on only one surface of the lead. Paddle leads may be desirable in certain situations because they provide more direct stimulation to a specific surface and require less energy to produce a desired effect. Because paddle leads are larger than percutaneous leads, they have historically required surgical implantation through a procedure known as partial laminectomy that requires the resection and removal of vertebral tissue.

Paddle leads have limited torsional stiffness and bending rigidity. As a result, physicians use various dissection tools to open a space in the tissue prior to attempting to implant paddle leads at the desired site. The dissection tool must have sufficient stiffness to open the tissue, while not creating excess pressure on the spinal cord or nerve roots. After the space is opened a second tool or blank is then typically inserted to verify that the space created is sufficient to accommodate the paddle lead.

Even with a space formed in the tissue to accept the paddle lead, paddle leads are difficult to manipulate and control as they are directed to their intended implantation site. As a result, surgeons typically create a space in the tissue greater than the size of the paddle lead to aid in implantation. The oversize space, however, results in imprecise positioning and subsequent migration of the paddle lead within the patient.

BRIEF SUMMARY

The present disclosure is directed to a combination dissection tool and blank that provides sufficient column strength to separate fatty tissue to create a space for the therapy delivery element, while having sufficient flexibility and surface area to minimize pressure on the spinal cord or nerve roots. The present dissection tool and blank has a maximum cross-sectional area substantially the same as a maximum cross-sectional area of the paddle lead being implanted, reducing the risk of creating an oversized space.

One embodiment is directed to a combined dissection tool and blank for implanting a paddle lead having an electrode portion and a lead body. The combined dissection tool and blank includes a blank with a maximum cross-sectional area substantially equal to a maximum cross sectional area of the electrode portion of the paddle lead. An elongated body portion is attached to the blank. A guide wire extends through the body portion substantially to a distal end of the blank. The guide wire provides sufficient column strength to separate fatty tissue to create a space for receiving the paddle lead.

In one embodiment, the guide wire is embedded in the body portion and the blank. In another embodiment, the guide wire is inserted in a lumen that extends through the body portion and substantially through the blank. A plurality of guide wires sized to fit in the lumen are optionally include. The guide wires preferably have different stiffness, column strength, geometries, cross-sectional shapes, and flexibility. The blank optionally includes a distal end configured to cut tissue.

In one embodiment, the blank includes a maximum width and a maximum thickness substantially the same as a maximum width and maximum thickness of the paddle lead. In another embodiment, the blank includes a maximum width and a maximum thickness each are within less than about +/−15%, or less than about +/−10%, or less than about +/−5% of a maximum width and a maximum thickness of the paddle lead. In another embodiment, the blank includes a maximum cross-sectional area within less than about +/−15%, less than about +/−10%, or less than about +/−5% of a maximum cross-sectional area of the paddle lead.

In another embodiment, the blank is slightly smaller than the electrode portion of the paddle lead to better secure the paddle lead in the tissue. In one embodiment, the maximum width and the maximum thickness of the blank are each less than the maximum width and the maximum thickness of the paddle lead, respectively, by within about 15% or less, or within about 10% or less, or within about 5% or less. In another embodiment, the blank includes a maximum cross-sectional area that is less than a maximum cross-sectional area of the paddle lead by within about 15% or less, or within about 10% or less, or within about 5% or less.

The guide wire optionally includes a non-circular cross-sectional shape. In one embodiment, a portion of the guide wire extending along the blank includes a non-circular cross-sectional shape configured to permit flexure generally perpendicular to a major surface of the blank, while inhibiting flexure parallel to the major surface of the blank.

The present disclosure is also directed to a neurostimulation system. The neurostimulation system includes an implantable pulse generator and a paddle lead with an electrode portion and a lead body. A combined dissection tool and blank is provided to create a path though tissue to implant the paddle lead. The blank has a maximum cross-sectional area substantially equal to a maximum cross sectional area of the electrode portion of the paddle lead. An elongated body portion is attached to the blank. A guide wire extends through the body portion substantially to a distal end of the blank. The guide wire provides sufficient column strength to separate fatty tissue to create a space for receiving the paddle lead.

The present disclosure is also directed to a a method of implanting a paddle lead in a living body. The method includes the step of selecting a dissection tool and blank with a blank having a maximum cross sectional area substantially equal to a maximum cross section area of the paddle lead. A guide wire extends through the body portion to substantially a distal end of the blank. The guide wire provides sufficient column strength to separate fatty tissue to create a space for receiving the paddle lead. The blank is advanced into the living body to create a path to an implantation site. The dissection tool and blank is then removed from the living body and the paddle lead is steered along the path to the implantation site. A proximal end of the paddle lead is electrically coupled to an implantable pulse generator located in the living body.

In one embodiment the guide wire is removable. The blank is advanced partway to the implantation site. The first guide wire is then removed and a different guide wire substituted. The blank is then advanced to the implantation site.

BRIEF DESCRIPTION OF THE SEVERAL VIEWS OF THE DRAWINGS

FIG. 4 illustrates a kit including a dissection tool and blank and a corresponding paddle lead in accordance with an embodiment of the present disclosure.

FIGS. 5A and 5B illustrate an alternate dissection tool and blank in accordance with an embodiment of the present disclosure.

FIGS. 6A and 6B illustrate an alternate kit including a paddle lead and a dissection tool and blank in accordance with an embodiment of the present disclosure.

FIGS. 7A-7E illustrate alternate configurations of dissection tool and blank and corresponding paddle leads in accordance with an embodiment of the present disclosure.

DETAILED DESCRIPTION OF SOME EMBODIMENTS

The description that follows relates to spinal cord stimulation (SCS) system. However, it is to be understood that the while the present disclosure lends itself well to applications in SCS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

In another embodiment, one or more of the therapy delivery elements may be a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be an electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, and any combination thereof. "Target tissue site" refers generally to the target site for implantation of a therapy delivery element, regardless of the type of therapy.

Figure 1:
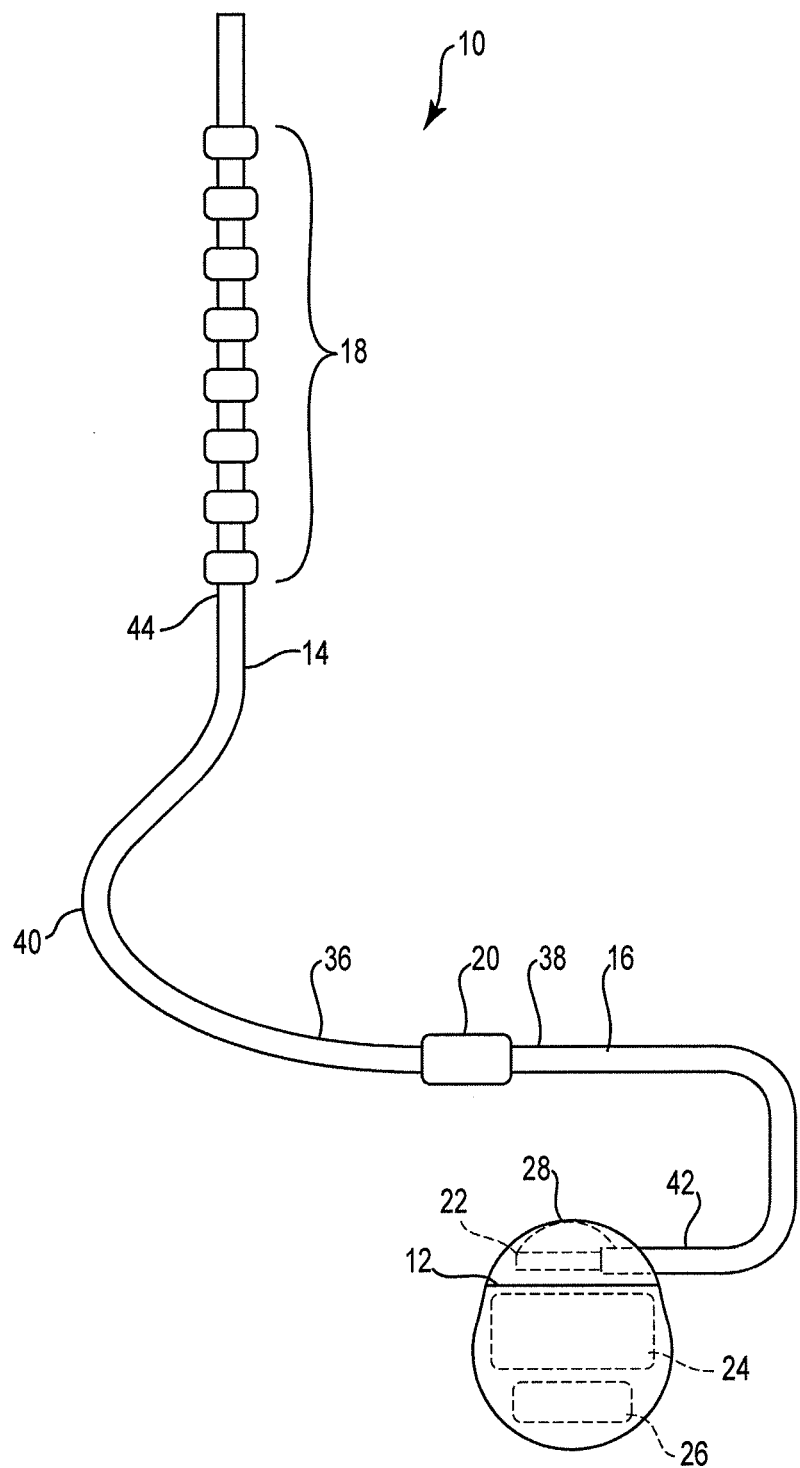
FIG. 1 is a schematic illustration of a therapy delivery system.

FIG. 1 illustrates a generalized therapy delivery system 10 that may be used in spinal cord stimulation (SCS), as well as other stimulation applications. The therapy delivery system 10 generally includes an implantable pulse generator 12, an implantable therapy delivery element 14, which carries an array of electrodes 18 (shown exaggerated for purposes of illustration), and an optional implantable extension lead 16. Although only one therapy delivery element 14 is shown, typically two or more therapy delivery elements 14 are used with the therapy delivery system 10.

The therapy delivery element 14 includes elongated body 40 having a proximal end 36 and a distal end 44. The elongated body 40 typically has a diameter of between about 0.03 inches to 0.07 inches and a length within the range of 30 cm to 90 cm for spinal cord stimulation applications. The elongated body 40 may be composed of a suitable electrically insulative material, such as, a polymer (e.g., polyurethane or silicone), and may be extruded from as a uni-body construction.

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector 22 associated with housing 28. Alternatively, the proximal end 36 of the therapy delivery element 14 can be electrically coupled directly to the connector 20.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 are protected from the body tissue and fluids. The connector 22 is disposed in a portion of the housing 28 that is, at least initially, not sealed. The connector 22 carries a plurality of contacts that electrically couple with respective terminals at proximal ends of the therapy delivery element 14 or extension lead 16. Electrical conductors extend from the connector 22 and connect to the electronic subassembly 24.

Figure 2:
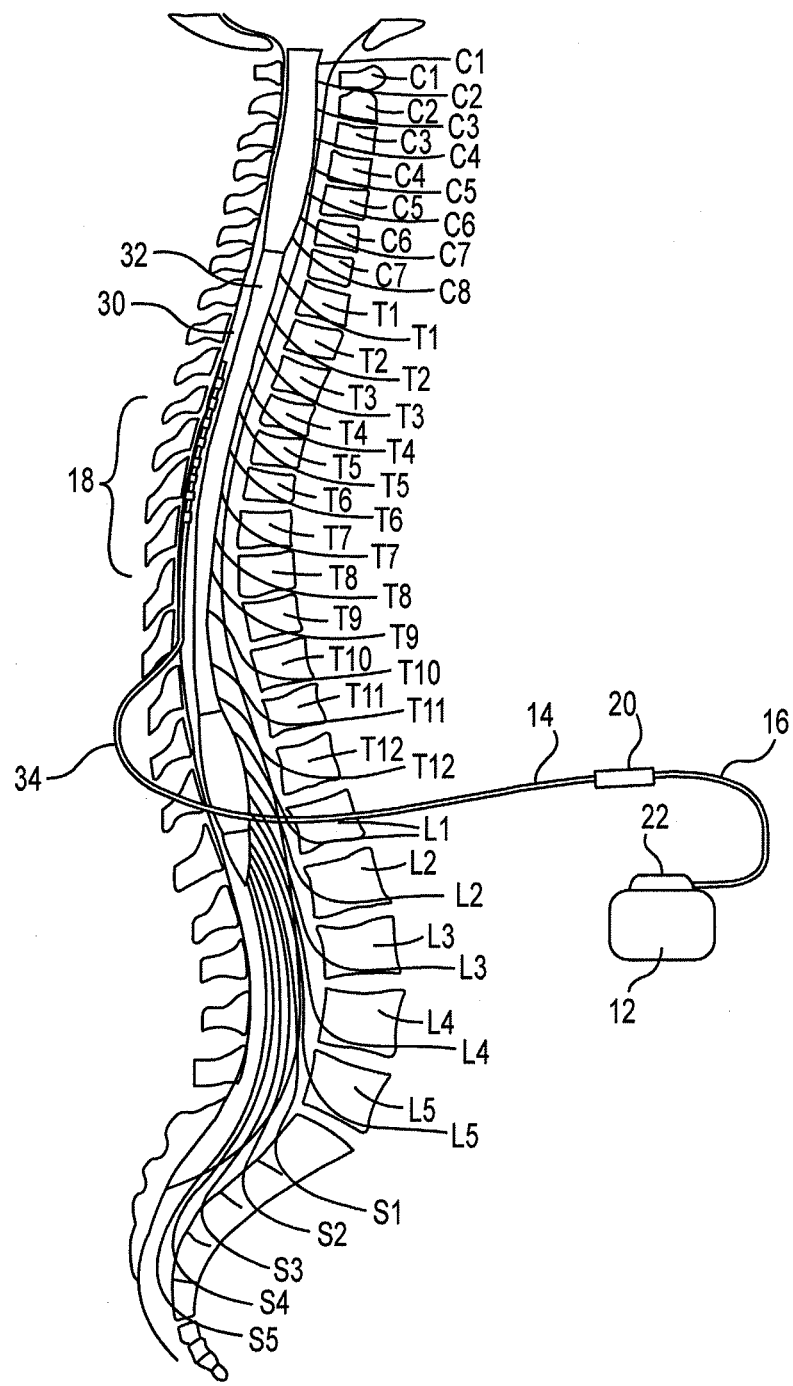
FIG. 2 is a schematic illustration of an environment for a therapy delivery system in accordance with an embodiment of the present disclosure.

FIG. 2 is a side skeletal view of a human body illustrating spinal column. The sacrum region is at a lower end of the spinal column below L-5 and adjacent the pelvic region. The sacrum is a triangular-shaped bone formed generally by five fused vertebrae, i.e., sacral vertebrae that are wedged dorsally between the two hip bones of the pelvic region in this region of the human anatomy. The lumbar region extends from L-1 to L-5 between the sacrum region at a lower end and the thorax region (T-1 to T-12) at an upper end. The thorax region extends from T-12 to T-1 at the base of the cervical region. The cervical region extends from C1 to C7.

The therapy delivery element 14 is implanted in the epidural space 30 of a patient in close proximity to the dura, the outer layer that surrounds the spinal cord 32, to deliver the intended therapeutic effects of spinal cord electrical stimulation. The target stimulation sites 49 (see e.g., FIG. 3) may be anywhere along the spinal cord 32, such as for example proximate the sacral nerves.

Figure 3:
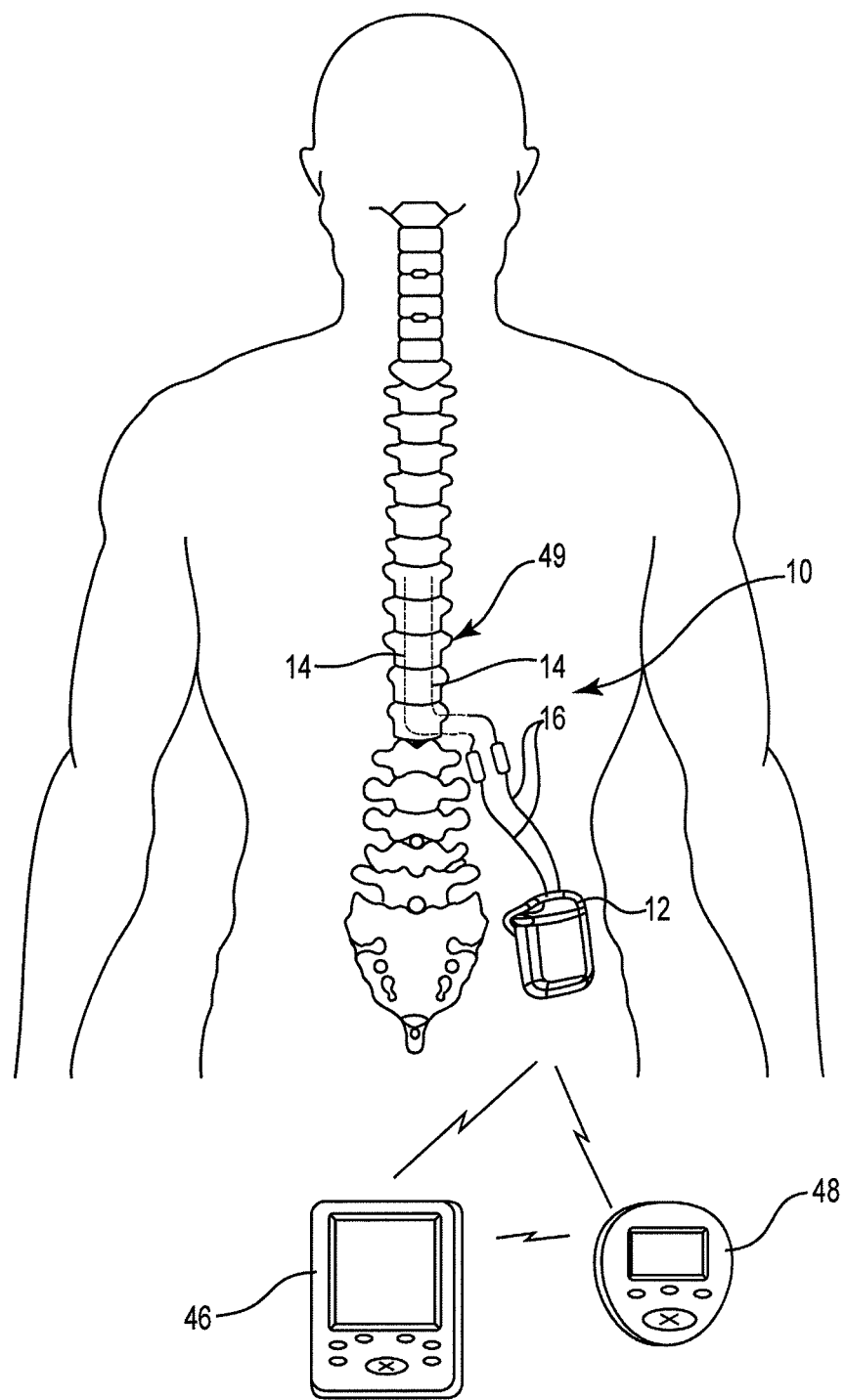
FIG. 3 is an alternate illustration of the environment for an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 3. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector 22 of the implantable pulse generator 12, since different manufacturers use different connectors at the ends of their stimulation leads and are not always compatible with the connector 22.

As illustrated in FIG. 3, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 48, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

FIG. 4 illustrates lead kit 100 including a combined dissection tool and blank 102 and corresponding paddle lead 104 in accordance with an embodiment of the present disclosure. The paddle lead 104 includes an electrode portion 106 with a plurality of electrodes 108 and a lead body 110. The electrodes 108 may be recessed or coplanar relative to surface 112 of the electrode portion 106. For example, the electrodes 108 may be recessed about 0.010 inches or 0.25 millimeters ("mm") from the surface 112.

The lead body 110 contains wires that electrically couple the electrodes 108 to an implantable pulse generator (see e.g., FIG. 1). Various lead body constructions are disclosed in commonly-assigned application Ser. No. 13/220,913, entitled Lead Body with Inner and Outer Co-Axial Coils, filed Aug. 30, 2011 and Ser. No. 13/045,908, entitled Implantable Lead with Braided Conductors, filed Mar. 11, 2011, both of which are hereby incorporated herein by reference in their entirety.

The electrode portion 106 includes a length 114, a width 116 and a thickness 118. For example, the electrode portion 106 may have a nominal length 114 of about 8 inches (20 cm), a nominal width 116 of about 0.15 inches (3.8 mm), and a nominal thickness 118 of about 0.04 inches (1 mm). A variety of other electrode portions can be used with the present disclosure, such as disclosed in U.S. Pat. No. 6,978,180, which is incorporated herein by reference in its entirety. The electrode portions 106 is typically constructed from a polymeric material, such as for example, polyurethane or silicone, or an alloy of silicone and polyurethane have a durometer ranging between about 20 to about 90, and between about 40 and about 70, and between about 50 to about 60, as measured according to ASTM D2240, type A.

The paddle lead 104 is illustrated with removable stylet 120 located in a lumen that extends substantially to distal end 122 of the electrode portion 106. The stylet 120 provides steerability, rigidity, and column strength to both the lead body 110 and the electrode portion 106 to facilitate insertion of the paddle lead 104 into a patient. In some embodiments, the stylet 120 can include one or more bends that steer or direct the more flexible elongated lead body 110 and electrode portion 106 to the target location. After the paddle lead 104 is implanted, the stylet 120 is removed.

The combination dissection tool and blank 102 includes a blank 130 with a maximum width 136 and a maximum thickness 138 substantially the same as the maximum width 116 and maximum thickness 118 as the electrode portion 106 on the paddle lead 104. In one embodiment, the maximum width 136 and the maximum thickness 138 of the blank 130 are about +/−15% or less, or about +/−10% or less, or about +/−5% or less than the maximum width 116 and the maximum thickness 118 of the electrode portion 106, respectively.

For example, where the maximum width 136 and the maximum thickness 138 of the blank 130 are each within about 10% or less of the maximum width 116 and the maximum thickness 118 of the electrode portion 106, if the electrode portion 106 has a width of about 3.8 mm and a thickness of about 0.04 mm, the blank 130 would have width of about 3.8 mm+/−0.38 mm (between about 3.42 mm to about 4.18 mm), and a thickness of about 0.04 mm+/−0.004 mm (between about 0.036 mm to about 0.044 mm).

In one embodiment, the blank 130 is preferably slightly smaller than the electrode portion 106, with the goal of forming an opening in the tissue smaller than the electrode portion 106. As a result, the electrode portion 106 is more secure in the desired location. The maximum width 136 and the maximum thickness 138 of the blank 130 are less than the maximum width 116 and the maximum thickness 118 of the paddle lead 104 by about 15% or less, or about 10% or less, or about 5% or less, respectively. For example, where the maximum width 136 and the maximum thickness 138 of the blank 130 are each about 10% less than of the maximum width 116 and the maximum thickness 118 of the electrode portion 106, if the electrode portion 106 has a width of about 3.8 mm and a thickness of about 0.04 mm, the blank 130 would have width between about 3.8 mm to about 3.42 mm, and a thickness between about 0.04 mm to about 0.036 mm.

In another embodiment, maximum cross-sectional area 144 of the blank 130 is the primary factor to the size of the space created during the implantation process. That is, as the dissection tool and blank 102 is advanced into the tissue the space formed corresponds to the maximum cross-section 144 of the blank 130. The maximum cross-sectional area 144 of the blank 130 is about +/−15% or less, or about +/−10% or less, or about +/−5% or less of maximum cross-sectional area 124 of the paddle lead 104. The maximum cross-sectional area of the blank 130 is preferably measured along a plane generally perpendicular to the direction of travel of the blank 130 into the patient. Although not necessarily required, the length 134 of the blank 130 may be similar to the length 114 of the paddle lead 104.

For example, if the electrode portion 106 has a width of about 3.8 mm and a thickness of about 0.04 mm, with a cross-sectional area of about 0.152 mm$^2$, the blank 130 has a cross-sectional area between about 0.1368 mm$^2$ to about 0.1672 mm$^2$.

In one embodiment, the cross-sectional area 144 of the blank 130 is preferably slightly smaller than the cross-sectional area 124 of the electrode portion 106. For example, the maximum cross-sectional area 144 of the blank 130 is less than the maximum cross-sectional area 124 of the paddle lead 104 by about 15% or less, or about 10% or less, or about 5% or less. For example, if the electrode portion 106 has a width of about 3.8 mm and a thickness of about 0.04 mm, with a cross-sectional area of about 0.152 mm$^2$, the blank 130 has a cross-sectional area between about 0.1368 mm$^2$ to about 0.152 mm$^2$.

Body portion 132 serves as the handle that is grasped by the surgeon. A separate handle can optionally be fixed to the proximal end of the body portion 132 to facilitate manipulation of the tool 102.

In the illustrated embodiment, one of the guide wires 140A, 140B ("140") is optionally positioned in lumen 142 in the dissection tool and blank 102. The guide wire 140 preferably extends substantially to distal end 146 of the blank 130. For example, the guide wire 140 is within about 0.100 inches to about 0.300 inches of the distal end 146.

The guide wires 140 have sufficient column strength to penetrate the tissue and reach the implantation location. The flexibility of the guide wire 140 combined with the surface area of the blank 130 minimizes pressure on the spinal cord and nerve roots. The guide wires 140 are typically made from stainless steel.

The guide wires 140A, 140B have different properties such as stiffness, column strength, flexibility, and the like. The different properties can be achieved by different geometries, cross-sectional shapes, dimensions, materials, and the like. The surgeon can select the guide wire 140 that best suits his needs or can used different guide wires during different phases of the implantation procedure. In an alternate embodiment, the guide wire 140 is molded or imbedded in the dissection tool and blank 102.

Distal end 146 of the blank 130 may have a configuration adapted to dissect subcutaneous tissue, whereas the distal end 122 of the paddle lead 104 is typically blunt. For example, the distal end 146 may include a cutting edge that is straight or serrated (see e.g., FIG. 5B). The blank 130 may be made from stainless steel, titanium, polyester, polyurethane, silicone, polysulfone and/or polycarbonate plastic, or other biocompatible materials. In some instances, all or a portion of the blank 130 may be coated, e.g., with Polytetrafluoroethylene (PTFE), to reduce friction with a patient's tissue during insertion. In one embodiment, the blank 130 has radiopaque properties to facilitate imaging during implantation. For example, the blank 130 can be impregnated with barium sulfate. In another embodiment, the guide wire 140 has radiopaque properties.

FIGS. 5A and 5B illustrate an alternate dissection tool and blank 150 with guide wire 152 having a non-circular distal portion 154 in accordance with an embodiment of the present disclosure. Distal portion 154 of the guide wire 152 is partially flattened to facilitate directional or preferential bending generally in direction perpendicular to flattened surface 162, but to resist bending generally in direction 160 parallel to the flattened surface 162.

The guide wire 152 is attached to the blank 150 corresponding to the size of the paddle lead so that flattened surface 162 is generally coplanar with plane 164 of blank 166. Consequently, the blank 166 bends more easily in a direction perpendicular to the plane 164, but resists bending generally in direction 168 parallel to the plane 164.

In the illustrated embodiment, the guide wire 152 extends above the top surface 164 of the blank 166. In one embodiment, the corresponding paddle lead includes a similar protrusion on the top surface of the electrode portion. For purposes of determining whether the blank 166 is substantially the same as the paddle lead, maximum cross-sectional area is preferred. In one embodiment, the cross-sectional area of the blank 166 is rectangular.

FIGS. 6A and 6B illustrate kit 200 including a paddle lead 202 and a combined dissection tool and blank 204 in accordance with an embodiment of the present disclosure. The paddle lead 204 includes an electrode portion 206, a lead body 208 and a removable stylet 210. Corresponding dissection tool and blank 202 includes an embedded guide wire 212. In the illustrated embodiment, distal end 214 of the blank 216 on the dissection tool and blank 202 includes serrated cutting edge 218. For purposes of the present disclosure, however, the length and width of the blank 216 and the electrode portion 206 are considered substantially the same notwithstanding the serrated edge 218.

FIGS. 7A-7E illustrate alternate shapes for the combined dissection tool and blank, and the corresponding paddle lead. The various tip shapes facilitate introduction of the tools into the patient. Consequently, it is clear that the present disclosure is not limited by the shape of the paddle lead.

Figure 8:
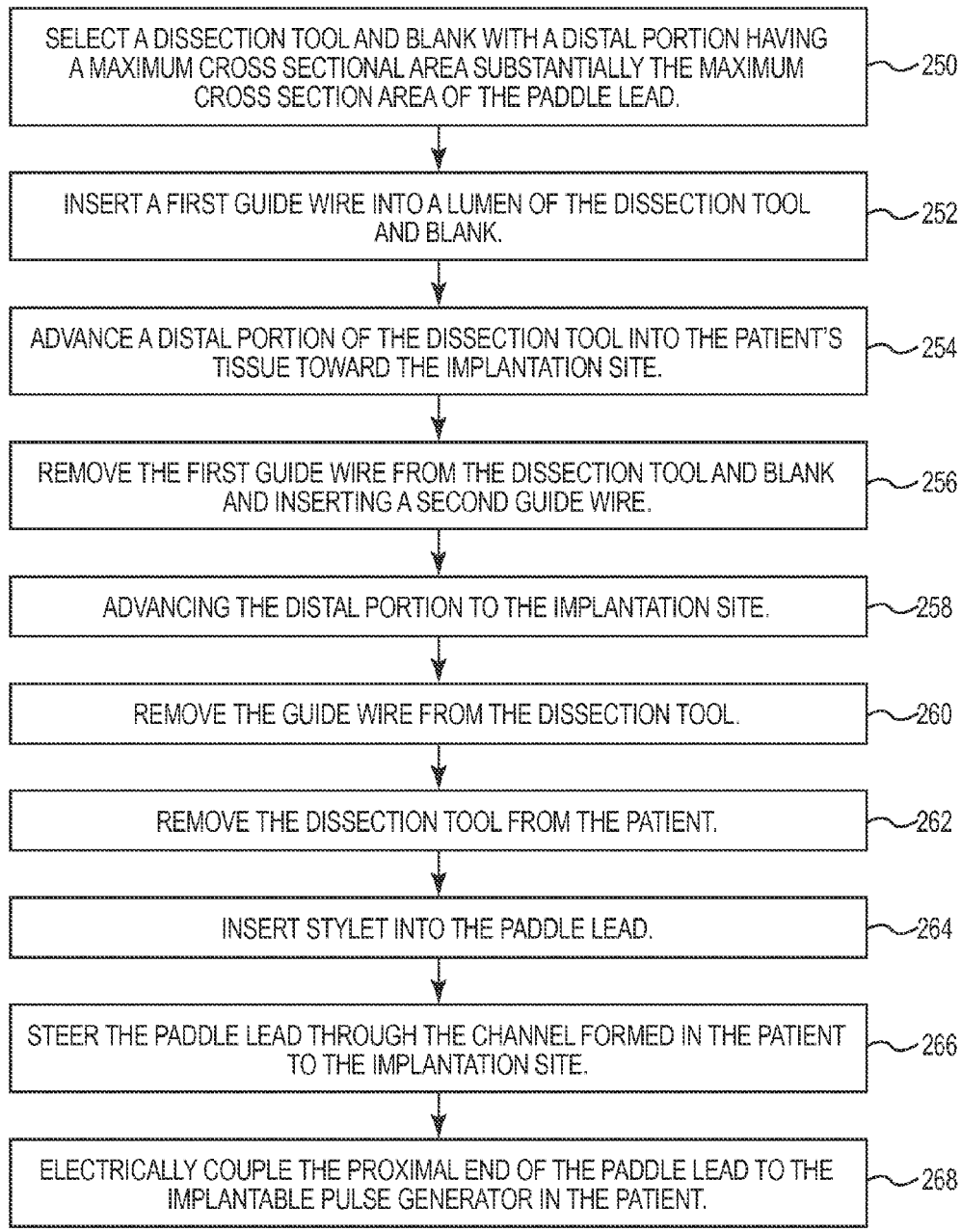
FIG. 8 is a flow diagram of a method of implanting a paddle lead using a corresponding dissection tool and blank in accordance with an embodiment of the present disclosure.

FIG. 8 is a flow diagram of a method of implanting a neurostimulation system within a living body using a dissection tool and blank in accordance with an embodiment of the present disclosure. A dissection tool and blank is selected with a blank having a maximum cross sectional area substantially equal to the maximum cross section area of the paddle lead (250). A first guide wire is inserted into a lumen of the combined dissection tool and blank (252). The blank of the dissection tool and blank is advanced into the patients tissue toward the implantation site (254). If greater force is required to penetrate the tissue, the first guide wire is removed and a second guide wire is inserted into the lumen (256). The blank is then advanced to the implantation site (258). Once the blank of the dissection tool and blank reaches the implantation site, the guide wire is removed from the lumen (260). The dissection tool and blank is then removed from the patient (262). A stylet is inserted in lumen of paddle lead (264). The physician grasps the elongated lead body and/or a stylet hub to steer the paddle lead to the desired location in the patient. The stylet is removed once the paddle lead is positioned (266). Proximal ends of the paddle lead is electrically coupled to an implantable pulse generator implanted in the living body (268).

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. A combined dissection tool and blank for implanting a paddle lead having an electrode portion and a lead body, the combined dissection tool and blank comprising:
   a blank comprising a maximum cross-sectional area substantially equal to a maximum cross sectional area of the electrode portion of the paddle lead;
   an elongated body portion attached to the blank; and
   a guide wire extending through the body portion and the blank generally to a distal end of the blank, wherein the guide wire provides sufficient column strength to separate fatty tissue to create a space for receiving the paddle lead, the guide wire including a flattened distal portion including a flattened surface, the flattened distal portion being wider than a remainder of the guide wire, the distal portion being configured to allow bending in a first direction perpendicular to the flattened surface and resist bending in a second direction parallel to the flattened surface.

2. The combined dissection tool and blank of claim 1, wherein the guide wire is molded within the body portion and blank.

3. The combined dissection tool and blank of claim 1, wherein the guide wire is selectively disposed within a lumen that extends through the body portion and substantially through the blank.

4. The combined dissection tool and blank of claim 3, comprising a plurality of guide wires sized to fit in the lumen, wherein at least two of the plurality of guide wires have at least one of a different stiffness, a different column strength, a different geometry, a different cross-sectional shape, and a different flexibility.

5. The combined dissection tool and blank of claim 1, wherein the blank comprises a distal end configured to cut tissue.

6. The combined dissection tool and blank of claim 1, wherein the blank comprises a maximum width and a maximum thickness substantially the same as a maximum width and maximum thickness of the paddle lead.

7. The combined dissection tool and blank of claim 1, wherein the blank comprises a maximum width and a maximum thickness, each within +/−10% or less of a maximum width and a maximum thickness of the paddle lead.

8. The combined dissection tool and blank of claim 1, wherein the blank comprises a maximum width and a maximum thickness, each within +/−5% or less of a maximum width and a maximum thickness of the paddle lead.

9. The combined dissection tool and blank of claim 1, wherein the blank comprises a maximum width and a maximum thickness, each less than a maximum width and a maximum thickness of the paddle lead by within 10% or less.

10. The combined dissection tool and blank of claim 1, wherein the blank comprises a maximum width and a maximum thickness, each less than a maximum width and a maximum thickness of the paddle lead by within 5% or less.

11. The combined dissection tool and blank of claim 1, wherein the blank comprises a maximum cross-sectional area within +/−10% or less of a maximum cross-sectional area of the paddle lead.

12. The combined dissection tool and blank of claim 1, wherein the blank comprises a maximum cross-sectional area less than a maximum cross-sectional area of the paddle lead within 10% or less.

13. The combined dissection tool and blank of claim 1, wherein the guide wire comprises a non-circular distal portion.

14. The combined dissection tool and blank of claim 1, wherein the guide wire extending along the blank comprises a non-circular distal portion configured to permit flexure generally perpendicular to a major surface of the blank, while inhibiting flexure parallel to the major surface of the blank.

15. The combined dissection tool and blank of claim 1, wherein:
   the blank includes a first length extending along a longitudinal axis of the combined dissection tool and blank; and
   the flattened distal portion of the guide wire includes a second length extending along the longitudinal axis, the second length being substantially equal to or less than the first length.

16. A neurostimulation system comprising:
   an implantable pulse generator;
   a paddle lead comprising an electrode portion and a lead body;
   a combined dissection tool and blank comprising:
      a blank comprising a maximum cross-sectional area substantially equal to a maximum cross sectional area of the electrode portion of the paddle lead;
      an elongated body portion attached to the blank; and
      a guide wire extending through the body portion to substantially a distal end of the blank, wherein the guide wire provides sufficient column strength to separate fatty tissue to create a space for receiving the paddle lead, the guide wire including a flattened distal portion including a flattened surface, the flattened distal portion being wider than a remainder of the guide wire, the distal portion being configured to allow bending in a first direction perpendicular to the flattened surface and resist bending in a second direction parallel to the flattened surface.

17. The neurostimulation system of claim 16, wherein the guide wire is selectively disposed within a lumen that extends through the body portion and substantially through the blank.

18. The neurostimulation system of claim 17, comprising a plurality of guide wires sized to fit in the lumen, wherein at least two of the plurality of guide wires have at least one of a different stiffness, a different column strength, a different geometry, a different cross-sectional shape, and a different flexibility.

19. The neurostimulation system of claim 16, wherein the blank comprises a distal end configured to cut tissue.

20. The neurostimulation system of claim 16, wherein the blank includes a maximum width and a maximum thickness substantially the same as a maximum width and maximum thickness of the paddle lead.

21. The neurostimulation system of claim 16, wherein a portion of the guide wire extending along the blank includes a non-circular cross-sectional shape configured to permit flexure generally perpendicular to a major surface of the blank, while inhibiting flexure parallel to the major surface of the blank.

22. The neuro stimulation system of claim 16, wherein:
   the blank includes a first length extending along a longitudinal axis of the combined dissection tool and blank; and
   the flattened distal portion of the guide wire includes a second length extending along the longitudinal axis, the second length being substantially equal to or less than the first length.

23. An apparatus for implanting a paddle lead including an electrode portion and a lead body, the apparatus comprising:
   a blank including a maximum cross-sectional area substantially equal to a maximum cross sectional area of the electrode portion of the paddle lead, the blank including a distal end configured to dissect tissue;

an elongated body portion attached to the blank; and a guide wire extending through the body portion and the blank to a point proximate a distal end of the blank, wherein the guide wire is configured to provide sufficient column strength to separate fatty tissue to create a space for receiving the paddle lead, the guide wire including a flattened distal portion including a flattened surface, the flattened distal portion being wider than a remainder of the guide wire, the distal portion being configured to allow bending in a first direction perpendicular to the flattened surface and resist bending in a second direction parallel to the flattened surface.

24. The apparatus of claim 23, wherein the guide wire is removably disposed within a lumen that extends through the body portion and substantially through the blank.

25. The apparatus of claim 24, comprising a plurality of guide wires sized to fit in the lumen, wherein at least two of the plurality of guide wires have at least one of a different stiffness, a different column strength, a different geometry, a different cross-sectional shape, and a different flexibility.

26. The apparatus of claim 23, wherein the distal end of the blank is configured to cut tissue.

27. A combined dissection tool and blank for implanting a paddle lead having an electrode portion and a lead body, wherein at least the electrode portion of the paddle lead extends along a first longitudinal axis, the combined dissection tool and blank comprising:

a blank extending along a second longitudinal axis and comprising a maximum cross-sectional area perpendicular to the second longitudinal axis, the maximum cross-sectional area of the blank being substantially equal to a maximum cross sectional area of the electrode portion of the paddle lead extending along the first longitudinal axis;

an elongated body portion attached to the blank; and a guide wire molded within and extending through the body portion and the blank generally to a distal end of the blank, wherein the guide wire provides sufficient column strength to separate fatty tissue to create a space for receiving the paddle lead, the guide wire including a flattened distal portion including a flattened surface, the flattened distal portion being wider than a remainder of the guide wire, the distal portion being configured to allow bending in a first direction perpendicular to the flattened surface and resist bending in a second direction parallel to the flattened surface.

28. The combined dissection tool and blank of claim 27, wherein:

the blank includes a first length extending along a longitudinal blank axis of the combined dissection tool and blank; and the flattened distal portion of the guide wire includes a second length extending along the longitudinal blank axis, the second length being substantially equal to or less than the first length.

* * * * *